(12) United States Patent
Dolle

(10) Patent No.: US 7,456,202 B2
(45) Date of Patent: Nov. 25, 2008

(54) MARKED MALEIMIDE COMPOUNDS, METHOD FOR PREPARING SAME AND USE THEREOF FOR MARKING MACROMOLECULES

(75) Inventor: Frederic Dolle, Gometz-le-Chatel (FR)

(73) Assignee: Commissariat a l'Energie Atomique, Paris (FR)

( * ) Notice: Subject to any disclaimer, the term of this patent is extended or adjusted under 35 U.S.C. 154(b) by 561 days.

(21) Appl. No.: 10/517,612

(22) PCT Filed: Jun. 30, 2003

(86) PCT No.: PCT/FR03/02028

§ 371 (c)(1), (2), (4) Date: Dec. 22, 2004

(87) PCT Pub. No.: WO2004/002984

PCT Pub. Date: Jan. 8, 2004

(65) Prior Publication Data

US 2005/0249662 A1 Nov. 10, 2005

(30) Foreign Application Priority Data

Jul. 1, 2002 (FR) ................... 02 08203

(51) Int. Cl.
- C07D 207/22 (2006.01)
- C07D 401/02 (2006.01)
- A61K 51/00 (2006.01)
- A61K 31/44 (2006.01)

(52) U.S. Cl. .......... 514/343; 514/422; 424/1.89; 546/278.7; 548/404

(58) Field of Classification Search .......... None
See application file for complete search history.

(56) References Cited

U.S. PATENT DOCUMENTS

| 4,735,792 A | 4/1988 | Srivastava |
| 5,242,680 A | 9/1993 | Chorev |

FOREIGN PATENT DOCUMENTS

| WO | 99 11590 | 3/1999 |

OTHER PUBLICATIONS

Wilbur D S: "Rediohalogenation of Protein: An Overview of Radionuclides, Labeling Methods, and Reagents for Conjugate Labeling" Bioconjugate Chemistry, American Chemical Society, vol. 3, No. 6, pp. 433-470, Nov. 1, 1992. XP000328382.

C-Y Shiue: "Synthesis of 18F-labelled N-(p-'18F! fluorophenyl)maleimide and its derivatives for labelling monoclonal antibody with 18F" Journal of Labelled Compounds and Radiopharmaceuticals, vol. 26, pp. 287-289, 1989. XP002091356.

*Primary Examiner*—Zinna N Davis
(74) *Attorney, Agent, or Firm*—Oblon, Spivak, McClelland, Maier & Neustadt, P.C.

(57) ABSTRACT

Fluorine-18-labelled maleimide compounds of general formula (I):

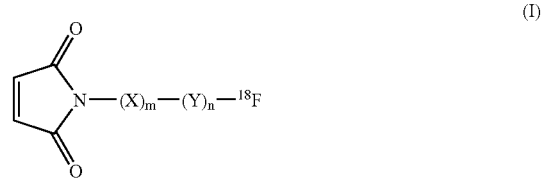

in which:
- m represents an integer from 0 to 10;
- n represents an integer from 1 to 10;
- Y represents a group selected from optionally substituted monocyclic or bicyclic heterocyclic groups;
- X represents a radical of formula:

$$(U)_a-((CR_1R_2)_b-(V)_c-((CR_3R_4)_e-(W)_f)_g-$$

in which:
- a, b, c, d, e, f and g represent each independently an integer from 0 to 10;
- U, V and W represent each independently $-NR_1-$, $-O-$, $-S-$,

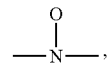

ethynyl, $-CR_1=CR_2-$, $-(C=O)-$, $-(C=S)-$, $-C(=NR_1)-$, $-C(=O)O-$, $-(C=S)S-$, $-C(=NR_1)NR_2-$, $-CR_1R_2-$, $-CR_1OR_2-$ or $-CR_1NR_2R_3-$.

Process for preparing these compounds; their use for labelling macromolecules, and complexes of these compounds with a macromolecule.

Detection and analysis kit, or diagnosis kit, comprising the said complexes.

Use of the complexes in a medical imaging process such as positron emission tomography (PET).

45 Claims, No Drawings

MARKED MALEIMIDE COMPOUNDS, METHOD FOR PREPARING SAME AND USE THEREOF FOR MARKING MACROMOLECULES

This application is a 371 of PCT/FR03/02028 filed Jun. 30, 2003.

The present invention pertains to maleimide compounds labelled with fluorine-18.

The invention also concerns a process for preparing these compounds.

The invention relates, finally, to the use of these maleimide compounds, especially fluorine-18-labelled maleimide compounds, for labelling macro-molecules, such as oligonucleotides, proteins, antibodies and peptides.

The technical field of the invention may be defined in a general manner as being that of the radio-labelling of macromolecules and, in particular, of proteins and peptides.

The reason for this is that, for use in research or diagnosis, macromolecules, such as proteins or else peptides, can be coupled with a labelling molecule which allows them to be detected; this labelling molecule may be, for example, a fluorescent molecule, gold particles, a paramagnetic compound or a molecule bearing a radioelement.

Proteins have been radioactively labelled with radioisotopes, iodine and various radioisotopes of metals, such as technetium, indium and gallium. More recently proteins have been labelled with fluorine-18.

For example, peptides coupled to radioelements, such as fluorine, allow in vivo detection of the location of thrombotic zones in the event of vascular accidents of any kind, especially inflammatory and apoptotic foci, using imaging systems.

Thus radioactive atoms which are short-lived positron emitters, and especially $^{18}F$, may in particular be detected by positron emission tomography (PET) instruments.

Owing in particular to the very short half-life of fluorine-18 (in the region of 109.8 minutes), radio-labelling with fluorine-18 poses specific problems, which make fluorine-18 labelling fundamentally different from labelling with the other halogens, such as iodine.

The aforementioned coupling may be carried out by any of the conventional techniques of organic chemistry that are known to the skilled person, and by the synthesis of peptide and protein labels which bear one or more short-lived radioactive atoms, especially $^{18}F$. This label is generally composed, on the one hand, of a moiety capable of receiving, for example, an $^{18}F$ atom and, on the other hand, of a moiety comprising any conventional function for binding to the macromolecule: for example, to the protein.

These labels must meet the demand for rapid and easy synthesis, since, owing to the short lifetime of radioisotopes such as $^{18}F$, the synthesis time must not generally exceed a few hours.

Moreover, owing to the high radioactivity of the compounds employed, this synthesis must be able to be carried out by robotic means.

Thus processes for labelling proteins or peptides with fluorine-18 employ labels which are also called labelled synthons or conjugates, and which are placed in three major classes according to whether they react with the amine groups, the sulphhydryl groups or the carbohydrate groups of the macromolecules, such as the proteins and peptides.

Among the compounds or conjugates which react with amino groups mention may be made of imidates, such as 3-[$^{18}F$]fluoro-5-nitrobenzoimidate, which react, for example, with the ε-$NH_2$ group of lysine in order to bind to a protein; activated esters, such as N-succinimidyl [$^{18}F$]fluorobenzoate; carboxylic acids, such as N-(4-[$^{18}F$]fluorobenzoic)acid; aldehydes, such as 4-[$^{18}F$]-pentafluorobenzaldehyde; and isothiocyanates, such as 4-([$^{18}F$]fluoromethyl)phenyl isothiocyanate.

Activated halides, such as 4-[$^{18}F$]fluorophenacyl bromide, react with amino groups, such as the ε-$NH_2$ group of lysine or the —SH group of cysteine.

Amines, such as 1-(4-([$^{18}F$]fluoromethyl)-benzoyl)aminobutane-4-amine, react with the $CO_2H$ groups, for example of glutamic acid or of aspartic acid, or with the CHO groups of glycoproteins.

Nitrenes with active photochemical centres, such as azidophenacyl [$^{18}F$]fluoride, also react with amino groups, for example the ε-$NH_2$ group of lysine.

The most effective and most widely described process for labelling proteins and peptides is that employing activated acids, but it is also the process which exhibits the greatest non-specificity, since all of the nucleophilic sites of the amino acids of the proteins or peptides will react with the label, conjugate, or labelled synthon.

Two more specific processes for labelling peptides and nucleotides exhibit high specificity in respect of sulphur atoms, such as those of cysteine, for example, for the peptides, and of a phosphorothioate function, for the nucleotides.

These are, firstly, processes employing halo-acetamide synthons, which, although satisfactory, exhibit the drawback of being very slow and hence poorly suited to $^{18}F$, owing to the half-life of the latter.

These are; further, processes employing activated maleimides, which are able to attach to the SH groups with a very high specificity, since the reaction is very slow with respect, for example, to the ε-$NH_2$ sites of lysine.

The scheme of the reaction involving the maleimido group is as follows, in the case of a protein:

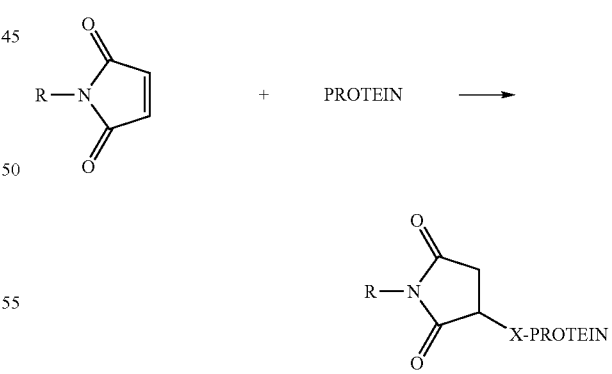

in which X represents —S—.

For any labelling, of whatever type, the molecules comprising a maleimide radical are presently considered as being the best, in terms of their reactivity with macromolecules, such as peptides or proteins.

The document of Shiue C.-Y. et al., J. Label. Compounds Radiopharm. 26: 287-289 (1989), describes the following compounds:

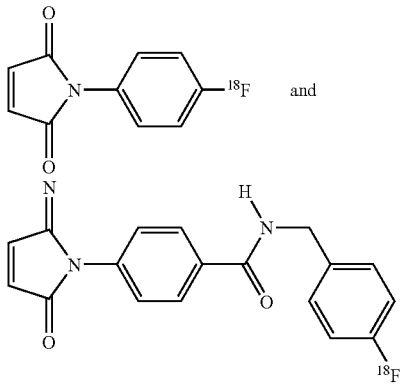

The first of these compounds is not easy to label with fluorine-18 with high specific activity.

This is because only fluorine $F_2$ would allow ready labelling (as with iodine), and in fact it turns out to be the case that $F_2$ is generally a product with low specific activity.

In particular, $F_2$ is not suitable for the manufacture of radiotracer compounds, which are, preferentially, a subject of the invention, for the simple reason that the injected mass of labelled molecule becomes substantial and that, in that case, the basic principle governing this tracer, namely the extremely low occupancy (for example, less than 5%) of the receptor sites, is not respected.

Moreover, the synthesis of the first of these compounds is difficult: it is, in effect, carried out in four steps, involving a substantial duration, with very low yields, and relatively complex chemical conversions. This process is therefore not amenable to easy automation.

The second of the compounds cited in the Shiue et al. document contains an amide chain, which is chemically not very robust and which is readily cleaved, or broken, in vivo.

Accordingly its use for diagnostic applications cannot be considered. Moreover, the synthesis of this second compound comprises three steps and the final yield is low: in the region, for example, of 10% (EOB: end of bombardment, i.e. end of irradiation).

Document U.S. Pat. No. 4,735,792 relates to molecules of formula:

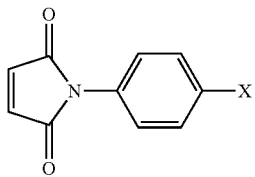

in which X is a radioactive halogen selected from bromine-75, bromine-76, bromine-82, iodine-123, iodine-125, iodine-131 and fluorine-18.

However, the only molecule actually prepared is that labelled with iodine-125.

The preparation of a fluorine-18-labelled molecule is neither mentioned nor evidenced, and the comments already made above, with regard to the first compound in the Shiue et al. document, also apply in the context of the document U.S. Pat. No. 4,735,792.

The skilled person, on reading this document, is not in possession of any information that would allow him or her specifically to prepare a fluorine-18-labelled compound, and, if he or she intends doing so, he or she would employ $F_2$ and hence would end up with a compound of low specific activity, unsuitable for use in PET imaging.

It may be borne in mind, moreover, that the chemistry employed for manufacturing the fluoro compound of the document U.S. Pat. No. 4,735,792 is complex and long.

There is therefore a need for fluorine-18-labelled maleimide compounds which exhibit high reactivity, high selectivity and a good specific activity.

There is also a need for fluorine-18-labelled maleimide compounds which can be manufactured in a high yield by a process which is simple, reliable, readily automatable, robotizable, rapid and of short duration.

The object of the present invention is to provide a fluorine-18-labelled maleimide compound which meets these needs, among others.

A further object of the present invention is to provide a fluorine-18-labelled maleimide compound which does not exhibit the drawbacks, deficiencies, limitations and disadvantages of the prior art compounds and which solves the problems of the prior art.

This object and other, further objects are achieved, in accordance with the invention, by providing a compound of general formula (I):

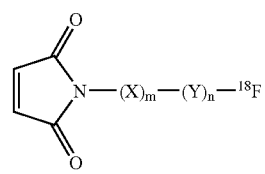

in which:
  m represents an integer from 0 to 10, such as 0, 1, 2, 3, 4, 5, 6, 7, 8, 9 or 10;
  n represents an integer from 1 to 10, such as 1, 2, 3, 4, 5, 6, 7, 8, 9 or 10;
  Y represents a group selected from mono-cyclic or bicyclic heterocyclic groups selected from imidazolyl, pyrazolyl, benzimidazolyl, pyridinyl, pyridazinyl, pyrimidinyl, pyrazinyl, triazinyl, quinolinyl, isoquinolinyl, cinnolinyl, quinazolinyl, quinoxalinyl and purinyl groups, it being possible for Y, optionally, to be substituted by one or more substituents, each of these substituents being selected independently from hydrogen, halogens (not radioactive), phenyl, $C_1$-$C_6$ alkyl, $C_1$-$C_6$ alkoxy, aryloxy, amino, mono- or di($C_1$-$C_6$ alkyl)amino, mono- or di(aryl)amino, thio, $C_1$-$C_6$ alkylthio, arylthio, formyl, $C_1$-$C_6$ alkyl-carbonyl, arylcarbonyl, carbonyl, $C_1$-$C_6$ alkoxy-carbonyl, aryloxycarbonyl, $C_1$-$C_6$ alkylaminocarbonyl, arylaminocarbonyl and trifluoromethyl groups;
  X represents a radical of formula:

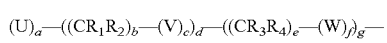

in which:
  a, b, c, d, e, f and g represent each independently an integer from 0 to 10, such as 0, 1, 2, 3, 4, 5, 6, 7, 8 or 9;
  U, V and W represent each independently —$NR_1$—, —O—, —S—,

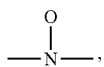

ethynyl, —CR$_1$=CR$_2$—, —(C=O)—, —(C=S)—, —C(=NR$_1$)—, —C(=O)O—, —(C=S)S—, —C(=NR$_1$)NR$_2$—, —CR$_1$R$_2$—, —CR$_1$OR$_2$— or —CR$_1$NR$_2$R$_3$—, where R$_1$, R$_2$, R$_3$ and R$_4$ are each independently selected from hydrogen, halogens, phenyl, C$_1$-C$_6$ alkyl, C$_1$-C$_6$ alkoxy, aryloxy, amino, mono- or di(C$_1$-C$_6$ alkyl)amino, mono- or di(aryl)amino, thio, C$_1$-C$_6$ alkylthio, arylthio, formyl, C$_1$-C$_6$ alkyl-carbonyl, arylcarbonyl, carbonyl, C$_1$-C$_6$ alkoxy-carbonyl, aryloxycarbonyl, C$_1$-C$_6$ alkylamino-carbonyl, arylaminocarbonyl and trifluoromethyl groups.

Generally in the present description halogen signifies fluorine, chlorine, bromine or iodine. C$_1$-C$_6$ alkyl corresponds to the branched-chain and linear-chain saturated hydrocarbon radicals having 1 to 6 carbon atoms, such as methyl, ethyl, propyl, butyl, pentyl and hexyl.

The heterocycles, aryl group, etc., may be attached and substituted in any position.

Similarly $^{18}$F may be attached to Y or X in any position, in particular in any position on a hetero-cycle.

Advantageously, in the compound of formula (I) above, n=1 and Y is a 3-pyridinyl group.

The compounds of formula (I) may belong to various classes; a first class may be defined as that of "alkyl ethers", which correspond to the formula (II) below:

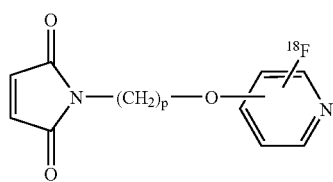

(II)

in which p is an integer from 1 to 10, such as 2, 3, 4, 5, 6, 7, 8 or 9, and

Preferred compounds of formula (II) are selected from the following compounds:

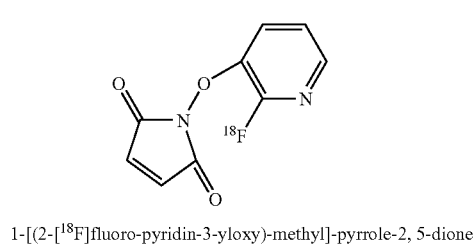

1-[(2-[$^{18}$F]fluoro-pyridin-3-yloxy)-methyl]-pyrrole-2, 5-dione

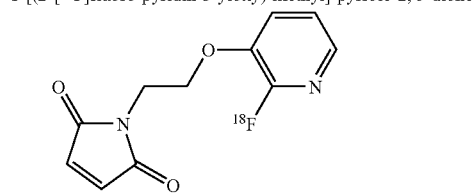

1-[2-(2-[$^{18}$F]fluoro-pyridin-3-yloxy)-ethyl]-pyrrole-2, 5-dione

-continued

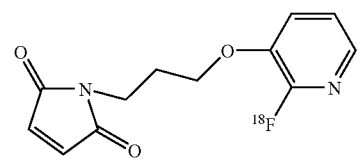

1-[3-(2-[$^{18}$F]fluoro-pyridin-3-yloxy)-propyl]-pyrrole-2, 5-dione

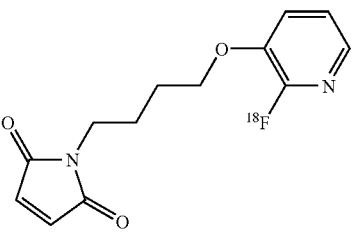

[1-[4-(2-[$^{18}$F]fluoro-pyridin-3-yloxy)-butyl]-pyrrole-2, 5-dione

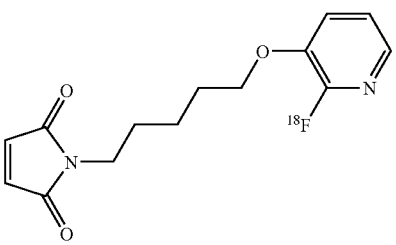

1-[5-(2-[$^{18}$F]fluoro-pyridin-3-yloxy)-pentyl]-pyrrole-2, 5-dione

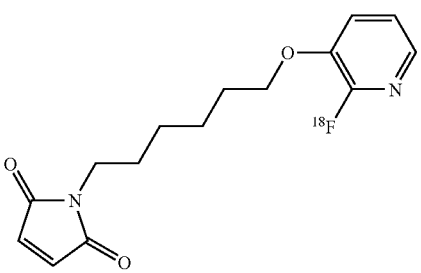

1-[6-(2-[$^{18}$F]fluoro-pyridin-3-yloxy)-hexyl]-pyrrole-2, 5-dione

A second class of compounds of formula (I) may be defined as those of "phenylalkyl ethers", which correspond to the formula (III) below:

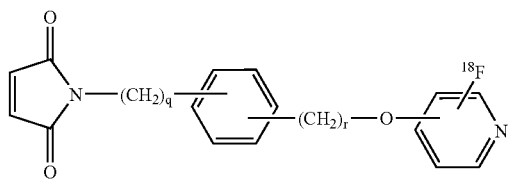

(III)

in which q and r represent independently an integer from 0 to 10, such as 0, 1, 2, 3, 4, 5, 6, 7, 8 or 9.

Preferred compounds of formula (III) are selected from the following compounds:

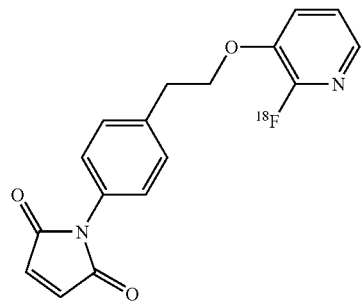

1-{4-[2-(2-[$^{18}$F]Fluoro-pyridin-3-yloxy)-ethyl]-phenyl}-pyrrole-2,5-dione

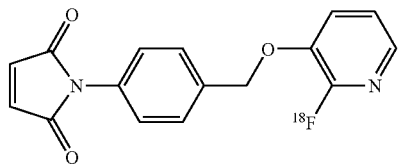

1-[4-(2-[$^{18}$F]Fluoro-pyridin-3-yloxymethyl)-phenyl]-pyrrole-2,5-dione

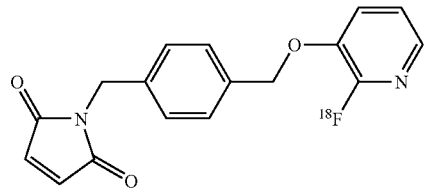

1-[4-(2-[$^{18}$F]Fluoro-pyridin-3-yloxymethyl)-benzyl]-pyrrole-2,5-dione

A third class is that of compounds which correspond to the formula (IV) below:

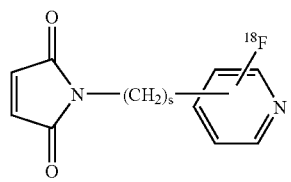

(IV)

in which s is an integer from 1 to 10, such as 2, 3, 4, 5, 6, 7, 8 or 9.

One preferred compound of formula (IV) is the following compound:

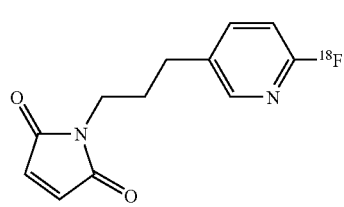

1-[3-(6-[$^{18}$F]Fluoro-pyridin-3-yl)-propyl]-pyrrole-2,5-dione

A fourth class is that of compounds which correspond to the formula (V) below:

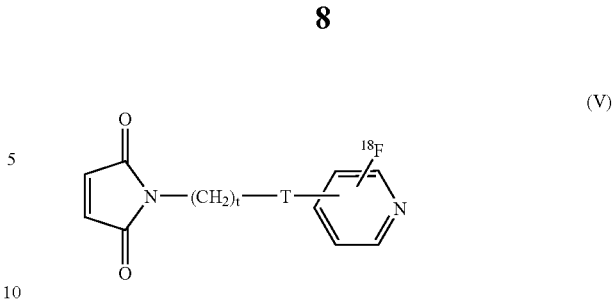

(V)

in which t is an integer from 0 to 10, such as 1, 2, 3, 4, 5, 6, 7, 8 or 9, and T is a —CH═CH— or —C≡C— group.

Preferred compounds of formula (V) are the following compounds:

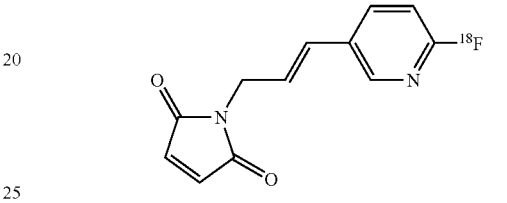

1-[3-(6-[$^{18}$F]Fluoro-pyridin-3-yl)-allyl]-pyrrole-2,5-dione

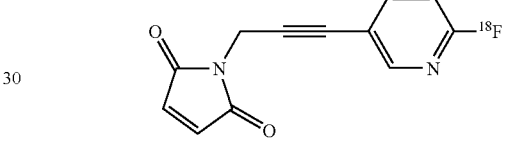

1-[3-(6-[$^{18}$F]Fluoro-pyridin-3-yl)-prop-2-ynyl]-pyrrole-2,5-dione

The compounds according to the invention have never been described nor disclosed in the prior art.

The compounds according to the invention differ fundamentally from the compounds of the prior art, owing to their specific structure, in which the moiety bearing the fluorine-18 atom is composed, according to the invention, of a specific group Y which is, in particular, a pyridinyl group; the binding moiety, for coupling to a macromolecule, such as a protein or a peptide, is composed, according to the invention, of a specific function, namely a maleimido function; and, finally, the moiety for binding to a macromolecule and the moiety bearing the fluorine-18 atom are connected, according to the invention, by a spacer arm or chain which is again specific, for example of alkyl type (generally 2 to 6C), alkyl ether type, phenylalkyl ether type or alkenyl type, which are not fragile and are not liable to in vivo rupture.

The invention provides for the use of a compound as described above for labelling macro-molecules.

This macromolecule may be any known macro-molecule, in particular a biological macromolecule, but it may be selected, for example, from oligonucleotides, proteins, antibodies and peptides. The said macro-molecule is advantageously a macromolecule for recognition of a specific site selected, preferably, from sites exhibiting target molecules which are specific of a disease, such as apoptosis sites, necrosis sites or tumour-area sites.

The invention likewise provides a complex comprising a macromolecule coupled to a compound according to the invention, as described above.

The said macromolecule is selected preferably from oligonucleotides, proteins, antibodies and peptides.

The said coupling is carried out by reacting the double bond of the maleimido group of the compound according to the invention with, specifically, an —SH (thiol) function of cysteine, in the case of a peptide, or a phosphorothioate function, in the case of an oligonucleotide.

This is one of the advantages associated with the specific structure of the compounds according to the invention, namely that of allowing specific, or even exclusive, labelling of cysteines, whereas the majority of other synthons allow only non-specific labelling of lysines and of cysteines.

The selective or even exclusive labelling of cysteines is due to the presence in the molecule of the invention of a "dedicated" function, namely the maleimido function, which is a dedicated function for chemoselectivity with regard to the thiols of cysteines, or, similarly, with regard to the phosphorothioate functions.

The labelling or coupling, via the cysteine, may be a direct labelling or coupling, in other words such that the cysteine already exists in the macro-molecule which it is desired to couple to the compound according to the invention; either cysteine or a molecule (peptide) comprising it may be introduced (coupled beforehand or not to the compounds of the invention) into the macromolecule which did not contain cysteine, and then the coupling is carried out, if it has not been carried out beforehand on the cysteine or the molecule comprising it.

The cysteine or molecule comprising it may, for example, be introduced "in a tailored fashion" into the macromolecule by protein/peptide engineering in a position in which it does not compete or interfere with the biological function.

The said macromolecule is advantageously a macromolecule for recognition of a specific site, as described above. The coupling, i.e. labelling, is preferably such that it does not affect the recognition activity of the target, the site, by the macromolecule.

The invention likewise provides a detection and analysis kit, for medical imaging, for example, comprising a compound according to the invention and a macromolecule.

The invention likewise provides a detection and analysis kit, for medical imaging, for example, comprising a compound according to the invention coupled to a macromolecule, in other words a complex according to the invention.

The invention also provides a diagnosis kit comprising a compound according to the invention and a macromolecule.

The invention further provides a diagnosis kit comprising a complex as described above.

The invention provides, finally, for the use of the complex or compound as described above in a medical imaging process, such as positron emission tomography (PET), and for the use of a complex or compound according to the invention for manufacturing a product intended for medical imaging, for example for positron emission tomography (PET).

Lastly the invention provides a product for medical imaging, especially positron emission tomography (PET), comprising a complex or a compound as described above and a pharmaceutically acceptable vehicle.

In their application, in the context of PET, the compounds and complexes according to the invention, comprising a fluorine-18 atom, exhibit numerous advantages over compounds with another radioactive halogen, for example iodine.

This is because the only positron-emitting isotope of iodine is iodine-124, which could allow PET.

However, it is still produced in small amounts (a few mCi as against curies for F-18). It is also difficult to produce. Finally, iodine-124 is not a pure positron emitter (in contrast to fluorine-18, 97%) and decays by beta+emission to only 25% and by electron capture to 75%; it possesses a large number of gamma rays, ranging from 0.603 MeV (62%) to 2.75 MeV (1%).

The invention likewise provides a process for preparing a compound of formula (I), as described above, in which:

a) a precursor compound of formula (Ia):

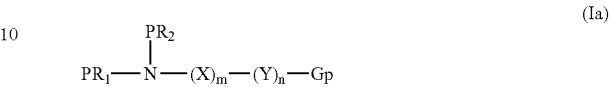

(Ia)

in which $PR_1$ and $PR_2$ represent independently a hydrogen atom or a protective group for the amine function, with the proviso that $PR_1$ and $PR_2$ are not both (simultaneously) a hydrogen atom, or else $PR_1$ and $PR_2$, together with the nitrogen atom, form a cyclic protective group for the amine function, Gp represents a leaving group capable of being replaced by a fluorine-18 atom, and X, Y, m and n are as already defined above, is contacted with a source of [$^{18}$F]-labelled fluoride ions F$^-$ to give a compound of formula (Ib):

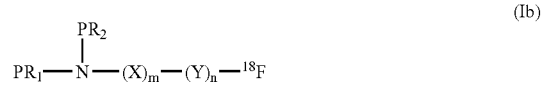

(Ib)

b) the protective group(s) $PR_1$ and/or $PR_2$ is or are removed from the amine function in the compound (Ib), to give a compound of formula (Ic):

(Ic)

c) the compound (Ic) is reacted with a reactant capable of giving a maleimido group from an amino group, to give the final compound of formula (I).

The process according to the invention is simple, reliable and easy to implement and can be easily robotized. It comprises only three steps, including one which is an extremely simple deprotection step.

The overall duration of the process is low: by way of example, it is generally from 60 to 120 minutes, preferably from 75 to 85 minutes.

The incorporation of the halogen, fluorine-18, is accomplished extremely effectively with a high yield, for example 70% to 100%, because, in particular, it is performed on a heterocyclic group, such as pyridine.

The final yield of the entirety of the process for a purified product is extremely high, for example from 15% to 25%, and the potential quantities of synthon compound, at the end of synthesis, are also very large.

In the compound (Ia) the groups $PR_1$ and $PR_2$, when they are protective groups, may be any protective group known in organic chemistry. They are preferably selected from the groups tert-butoxycarbonyl (BOC) and fluorenylmethoxycarbonyl (FMOC).

When $PR_1$ and $PR_2$, together with the nitrogen atom of the amine function, form a protective group for that function, this protective group may be, for example, a phthalimido group.

In the compound (Ia) the group Gp may be any leaving group capable of being replaced by an atom of fluorine-18; Gp is preferably selected from halogens, such as F, Cl, Br and I, mesyl, tosyl and triflate groups, when Y is an alkyl group; and Gp is preferably selected from halogens, ammonium salts, such as trimethylammonium trifluoromethanesulphonate, and the nitro group, when Y is an aromatic or heterocyclic group.

In step a) the source of $^{18}$F-labelled fluoride ions comprises the said fluoride ions and a counterion selected from large-sized cations, such as rubidium and tetrabutylammonium, and small-sized cations, such as potassium, sodium and lithium, the said small-sized cations being trapped, stabilized, for example, by a cryptand or a crown ether, etc., the said cryptand or crown ether being adapted to the small-sized cation employed.

One example of the cryptand is the product Kryptofix® $K_{222}$: (4,7,13,16,21,24-hexaoxa-1,10-diazabi-cyclo[8.8.8] hexacosane), which traps, for example, the potassium ion.

The counterion or cation may be brought into the form of any salt: for example, it may be $K_2CO_3$ in the case of potassium.

Step a) is generally carried out in a solvent, which may be any appropriate solvent, such as DMSO.

Step a) may be carried out under conditions known to the skilled person, with heating generally at a temperature from 50 to 200° C., for example, 145° C., for a time of generally from 1 to 30 minutes, for example from 4 to 6 minutes.

Step b), the step of removing the protective group from the amine function, i.e. the deprotection step, to give the compound of formula (Ic) in which the amino group is free, may be carried out by any known process of deprotection. It will be possible, for example, to contact the compound (Ib) with TFA in $CH_2Cl_2$ for a time of generally from 1 to 5 minutes, for example 2 minutes. It should be noted that TFA is generally used only if the protective group is removed in an acid medium, for example when $PR_1$=BOC and $PR_2$=H.

In step c) the reactant capable of giving a maleimido group from an amido group may be any known compound. It will therefore be possible for it to be selected from N-methoxy-carbonylmaleimide and succinimide.

Step c) may be carried out under conditions known to the skilled person, for example in a solvent such as xylene or THF, with heating generally at a temperature of from 100 to 200° C., for example 190° C., for a time of from 1 to 20 minutes, for example 5 minutes.

Step c) may in another embodiment also be carried out in a two-phase mixture, for example of dioxane and aqueous sodium bicarbonate, at ambient temperature for a time of from 3 to 15 minutes, for example 10 minutes; this embodiment of step c) offers the advantage of giving a better yield and of being implemented at ambient temperature, with no need to heat the mixture.

The compound of formula (Ia) may correspond to the formula (IIa) below:

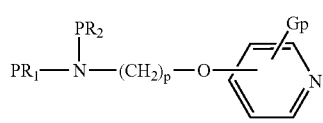

(IIa)

The compound (IIa) preferably corresponds to the formula (IIb) below:

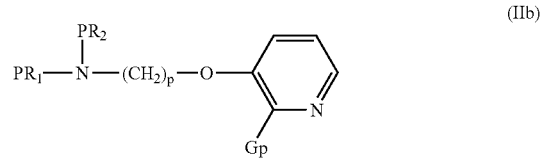

(IIb)

The compound of formula (Ia) may, in another embodiment, correspond to the formula (IIIa) below:

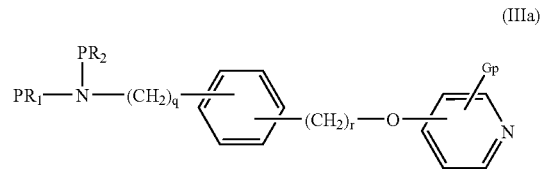

(IIIa)

The compound (IIIa) preferably corresponds to the formula (IIIb) below:

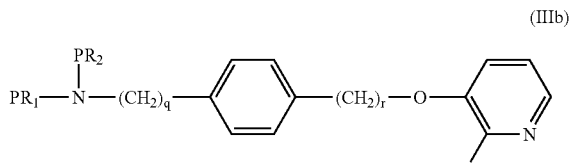

(IIIb)

The compound of formula (Ia) may, in yet another embodiment, correspond to the formula (IVa) below:

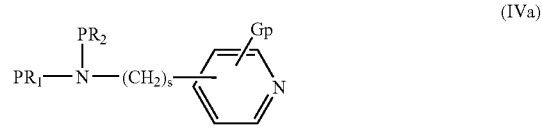

(IVa)

The compound (IVa) preferably corresponds to the formula (IVb) below:

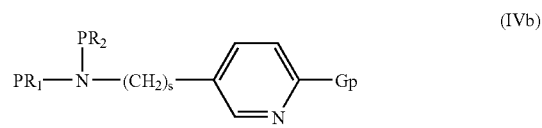

(IVb)

In another embodiment the compound of formula (Ia) may correspond to the formula (Va) below:

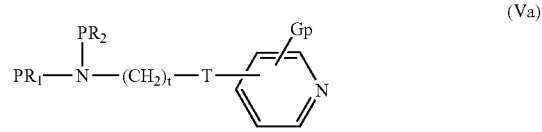

(Va)

The compound (Va) preferably corresponds to the formula (Vb) below:

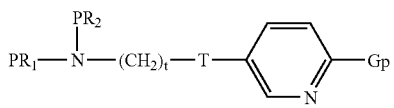

The invention likewise provides the precursor compounds of formulae (Ia), (IIa), (IIb), (IIIa), (IIIb), (IVa), (IVb), (Va) and (Vb), as described above, as synthesis intermediates for the compounds of formulae (I) to (V) according to the invention.

The precursor compounds may be selected in particular from the final compounds defined and set out above, in which the [$^{18}$F] is replaced by a non-radio-active halogen, such as $^{19}$F, Cl, Br or I, an ammonium salt, such as trimethylammonium trifluoromethane-sulphonate, or an NO$_2$ group and the 1-pyrrole-2,5-dione group is replaced by a tert-butoxycarbonylamino group.

Preferred precursor compounds are, for example, [3-(3-tert-butoxycarbonylaminopropoxy)pyridin-2-yl]-trimethylammonium trifluoromethanesulphonate and the tert-butyl ester of [3-(2-nitropyridin-3-yloxy)propyl]-carbamic acid.

The invention will now be set out in more detail in the description which follows, which is given by way of illustration and not of limitation, in relation to preparation examples of compounds according to the invention and of complexes according to the invention.

Experimental Conditions

Chemical products, thin-layer chromatography (TLC) and high-pressure liquid chromatography (HPLC).

The chemical products were obtained from a variety of suppliers (Aldrich, Fluka or Sigma France) and were used without further purification unless mentioned otherwise. The TLCs are carried out on plates precoated with silica gel 60F$_{254}$ from Merck. The compounds were located (1) if possible at 254 nm, using a UV lamp, and/or (2) by staining with iodine and/or (3) by immersing the TLC plates in an ethanolic 1% ninhydrin solution (or an aqueous 1% KMnO$_4$ solution) and by heating on a hot plate. The radioactive dots, marks or spots are detected using a Berthold Trace Master 20 automatic linear analysis instrument.

Spectroscopies

The chemical NMR spectra are recorded on a Bruker AMX instrument (300 MHz), using the hydrogen residue of the deuterated solvents (DMSO-d$_6$, δ: 2.50 ppm; CD$_2$Cl$_2$, δ: 5.32 ppm; CD$_3$OD, δ: 4.78; CD$_3$CN, δ: 1.93 ppm) and/or TMS as internal standards for $^1$H NMR, and the deuterated solvents (DMSO-d$_6$, δ: 39.5 ppm; CD$_2$Cl$_2$, δ: 53.8 ppm; CD$_3$OD, δ: 49.3 ppm) and/or TMS as internal standards for $^{13}$C NMR.

The chemical shifts are given in ppm with TMS (tetramethylsilane) as reference, the chemical shift of which is set at 0. s, d, t, dd, q, q5, m and b represent singlet, doublet, triplet, doublet of a doublet, quadruplet, quintuplet, multiplet, and broad, respectively. The mass spectra (MS) are measured on a Quadripolair Finnigan 4 600 instrument (DCI/NH$_4^+$).

Production of the Radioactive Isotope

Aqueous [$^{18}$F] fluoride ions were prepared in a CGR-MeV 520 cyclotron by irradiation of a 2 ml water target, using a 20 MeV proton beam on 95% [$^{18}$O]-enriched water by the nuclear reaction [$^{18}$O(p, n)$^{18}$F]. The fluoride ions were transferred into the appropriate shielded cell. Typical production: 550-650 mCi (20.3 to 24.0 GBq) of [$^{18}$F]F$^-$ at the end of bombardment for irradiation of 20 µA for 30 minutes (36 000 µC).

Miscellaneous

The radiosyntheses using fluorine-18, including the purifications by semi-preparative HPLC, were carried out in a 7.5 cm cell shielded with lead, using a computer-controlled Zymate robot system (from Zymack Corp., USA). Microwave activation is carried out with a Microwell 10 oven (2.45 GHz) supplied by Labwell AB, Sweden.

The specific radioactivity is determined as follows: the surface area of the UV absorption peaks, corresponding to the radiolabelled product, is measured on the HPLC chromatogram and compared with a calibration curve giving the mass as a function of the UV absorption.

EXAMPLE 1

General procedure for the Mitsunobu coupling of 3-(N-tert-butylcarbonylamino)-1-propanol with various 2-substituted 3-hydroxypyridine derivatives.

A solution of 3.0 g of triphenylphosphine (molecular mass: 262.69; 11.4 mmol) in THF (60 ml) is admixed with 1.8 ml of diethyl azodicarboxylate (DEAD, molecular mass: 174.16; d: 1.106; 11.4 mmol; 1 eq). After stirring at 0° C. for 10 to 15 minutes 1.95 ml of 3-(N-tert-butoxycarbonylamino)-1-propanol (molecular mass: 175.23; d: 1.025; 11.4 mmol; 1 eq) and the 2-substituted 3-hydroxypyridine derivative (11.4 mmol; 1 eq) are added. The mixture is stirred at ambient temperature overnight and then concentrated to dryness. The residue is taken up with CH$_2$Cl$_2$ and the solution obtained is washed with aqueous 10% NaHCO$_3$ solution, water and brine and dried with Na$_2$SO$_4$ before being concentrated to dryness. The residue is chromatographed on silica gel to give the desired derivative: 3-[3-(N-tert-butyloxycarbonylamino)-1-propoxy]pyridine (or tert-butyl ester of [3-(pyridin-3-yloxy) propyl]carbamic acid).

EXAMPLE 2

General procedure for deprotecting N-tert-butoxycarbonylamino functions with TFA.

From 3 to 7 mmol of the appropriate tert-butyl ester of [3-(pyridin-3-yloxy)propyl]carbamic acid in 5 ml of CH$_2$Cl$_2$ are admixed with 2 ml of TFA. The solution is stirred at ambient temperature for 45 minutes and concentrated to dryness.

The residue is redissolved in 2 ml of CH$_2$Cl$_2$ and again concentrated to dryness (twice) to give 3-(pyridin-3-yloxy) propylamine, in the form of an oily residue.

EXAMPLE 3

General procedure for forming the maleimido derivative.

From 2 to 3 mmol of the appropriate 3-(pyridin-3-yloxy) propylamine in 5 ml of THF are admixed in succession with 500 mg of maleic anhydride (molecular mass: 98.06; 5.1 mmol) and 200 mg of p-toluenesulphonic acid hydrate (molecular mass: 190.22; 1.0 mmol). The solution is refluxed for 24 hours and concentrated to dryness. The residue is chromatographed on silica gel to give the desired 1-[3-(pyridin-3-yloxy)propyl]-pyrrole-2,5-dione derivative.

EXAMPLE 4

Preparation of 2-fluoro-3-hydroxypyridine 100 ml of pyridine hydrofluoride (Py. (HF)$_x$, from Fluka, 70% of the sample consisting of hydrogen fluoride, 30% of the sample consisting of pyridine), cooled at 0° C., are admixed cautiously and in succession with 3.7 g of 2-amino-3-hydroxypyridine (molecular mass: 110.12; 33.6 mmol) and 3 g of NaNO$_2$ (molecular mass: 69.00; 43.5 mmol). The mixture is stirred at 0° C. for 1 hour and then slowly rendered basic with 10N aqueous NaOH solution, transferred to a decanter and extracted with EtOAc. The organic phases are combined, washed with water and brine, dried with Na$_2$SO$_4$ and concentrated to dryness. The residue is purified by passing it through a silica gel column (eluent: heptane/EtOAc: 50/50) to give 2.5 g (65%) of 2-fluoro-3-hydroxypyridine in the form of a solid, which is used without further purification.

Rf(EtOAc/heptane: 80/20): 0.65. m.p.: 131° C. $^1$H NMR (DMSO-d$_6$, 298 K): δ: 10.41 (s, 1H); 7.64 (td, J: 1.7 & 4.7 Hz, 1H); 7.42 (dd, J: 1.7, 1.7 & 10.8 Hz, 1H); 7.17 (ddd, J: 1.3, 4.7 & 7.8 Hz, 1H). $^{13}$C NMR (DMSO-d$_6$ 298 K): δ: 152.8 (d, $J^1_{F-C}$: 233 Hz, C); 140.2 (d, $J^2_{F-C}$: 27 Hz, C); 135.6 (d, $J^3_{F-C}$) 13 Hz, CH) 126.2 (d, $J^3_{F-C}$: 5 Hz, CH); 122.6 (CH).MS(DCI/NH$_4^+$): C$_5$H$_4$FNO: 131[M+NH$_4^+$]; 114[M+H$^+$]. Anal. (C$_5$H$_4$FNO) C, H, N.

EXAMPLE 5

In this example the preparation is described of a reference molecule, which is 1-[3-(2-fluoropyridin-3-yloxy)propyl] pyrrole-2,5-dione in which the fluorine is not radioactive fluorine but $^{19}$F.

a) Preparation of the tert-butyl ester of [3-(2-fluoropyridin-3-yloxy)propyl]carbamic acid The procedure described above in Example 1 is used, with the 2-fluoro-3-hydroxypyridine prepared in Example 4 (1.29 g; 11.4 mmol), to give 1.9 g (62%) of the tert-butyl ester of [3-(2-fluoropyridin-3-yloxy)-propyl]carbamic acid in the form of a yellow oil, after flash chromatography (eluent:pure CH$_2$Cl$_2$, heptane/EtOAc: 70/30 to 50/50).

Rf(CH$_2$Cl$_2$/EtOAc: 95/5): 0.45. $^1$H NMR (CD$_2$Cl$_2$, 298 K): δ: 7.68 (dt, J: 4.8 & 1.8 Hz, 1H); 7.28 (td, J: 7.8 & 1.5 Hz, 1H); 7.10 (dd, J: 5.1 & 0.9 Hz, 1H); 4.96 (b, w$_{1/2}$: 20 Hz, 1H); 4.07 (t, J: 6.0 Hz, 2H); 3.28 (q, J: 6.0 Hz, 2H); 1.98 (q$^5$, J: 6.0 Hz, 2H); 1.39 (s, 9H). $^{13}$C NMR (CD$_2$Cl$_2$, 298 K): δ: 156.3 (C); 154.1 (d, $J^1_{F-C}$: 235 Hz, C); 142.5 (d, $J^2_{F-C}$: 25 Hz, C); 137.5 (d, $J^3_{F-C}$: 13 Hz, CH); 123.0 (CH); 122.2 (CH); 79.2 (C); 67.3 (CH$_2$); 38.0 (CH$_2$); 29.8 (CH$_2$); 28.5 (CH$_3$).

b) Preparation of 3-(2-fluoropyridin-3-yloxy)-propylamine

The procedure described above in Example 2 is used, with the tert-butyl ester of [3-(2-fluoropyridin-3-yloxy)propyl] carbamic acid prepared in a) (1.0 g; molecular mass: 270.30; 3.7 mmol), to give 1.4 g (95%) of 3-(2-fluoropyridin-3-yloxy)propylamine.2TFA, in the form of a yellow oil.

$^1$H NMR (CD$_3$OD, 298 K): δ: 7.51 (bt, J<2.0 Hz, 1H); 7.36 (bt, J<3.0 Hz, 1H); 7.04 (bq, J<3.0 Hz, 1H); 4.03 (t, J: 6.0 Hz, 2H); 2.99 g (Q, J: 6.0 Hz, 2H); 2.01 (q$^5$, J: 6.0 Hz, 2H). $^{13}$C NMR (CD$_3$OD, 298 K): δ: 159.3 (q, $J^2_{F-C}$: 41 Hz, C, CF$_3$CO$_2$H); 155.3 (d, $J^1_{F-C}$: 237 Hz, C); 143.5 (d, $J^2_{F-C}$: 24 Hz, C); 138.5 (d, $J^3_{F-C}$: 13 Hz, CH); 125.1 (CH); 123.8 (CH); 116.4 (q, $J^1_{F-C}$: 284 Hz, C, CF$_3$, CO$_2$H); 67.9 (CH$_2$), 38.6 (CH$_2$); 29.4 (CH$_2$).

c) 1-[3-(2-Fluoropyridin-3-yloxy)propyl]-pyrrole-2, 5-dione

The procedure described above in Example 3 is used, with 3-(2-fluoropyridin-3-yloxy)propylamine.2TFA (1.0 g; molecular mass: 398.23; 2.5 mmol) to give 310 mg (48%) of 1-[3-(2-fluoropyridin-3-yloxy)propyl]-pyrrole-2,5-dione, in the form of a yellow powder, after flash chromatography (eluent: heptane/EtOAc: 50/50 to 30/70). For analytical purposes an aliquot fraction (100 mg) was purified again by preparative or semi-preparative HPLC.

Rf(EtOAc): 0.7. Rf(EtOAc/heptane: 80/20): 0.5. $^1$H NMR (CD$_2$Cl$_2$, 298 K): δ: 7.69 (bd, J: 3.0 Hz, 1H) 7.27 (t, J: 6.0 Hz, 1H); 7.11 (dd, J: 3.0 & 6.0 Hz, 1H); 6.69 (s, 2H); 4.05 (t, J: 6.0 Hz, 2H); 3.82 (t, J: 6.0 Hz, 2H); 2.11 (q$^5$, J: 6.0 Hz, 2H). $^{13}$C NMR (CD$_2$Cl$_2$, 298 K): δ: 171.2 (2×C); 154.0 (d, $J^1_{F-C}$: 235 Hz, C); 142.4 (d, $J^2_{F-C}$: 25 Hz, C); 137.7 (d, $J^3_{F-C}$: 13 Hz, CH); 134.5 (2×CH); 123.2 (CH); 122.2 (CH); 67.5 (CH$_2$); 35.4 (CH$_2$); 28.5 (CH$_2$). MS (DCI/NHR$^+$): C$_{12}$H$_{11}$FN$_2$O$_3$: 251 (M+H$^+$].

EXAMPLE 6

Preparation of the tert-butyl ester of [3-(2-nitropyridin-3-yloxy)propyl]carbamic acid The procedure described above in Example 1 is used, with 2-nitro-3-hydroxypyridine (1.6 g; molecular mass: 140.10; 11.4 mmol), to give 2.2 g (65%) of the tert-butyl ester of [3-(2-nitropyridin-3-yloxy)propyl]-carbamic acid in the form of a yellow oil, after flash chromatography (eluent: heptane/EtOAc: from 60/40 to 40/60). For analytical purposes an aliquot fraction (100 mg) is purified again on a preparative or semi-preparative HPLC apparatus.

Rf(EtOAc/heptane: 50/50): 0.35. $^1$H NMR (CD$_2$Cl$_2$, 298 K): δ: 8.04 (t, J: 3.0 Hz, 1H); 7.53 (d, J: 3.0 Hz, 2H); 4.95 (b, w$_{1/2}$: 15 Hz, 1H); 4.18 (t, J: 6.0 Hz, 2H); 3.26 (q, J: 6.0 Hz, 2H); 1.99 (q$^5$, J: 6.0 Hz, 2H); 1.40 (s, 9H). $^{13}$C NMR (CD$_2$Cl$_2$, 298 K): δ: 156.3 (C); 149.2 (C); 147.3 (C); 139.5 (CH); 129.2 (CH); 124.0 (CH); 79.2 (C); 68.3 (CH$_2$); 37.9 (CH$_2$); 29.5 (CH$_2$); 28.4 (CH$_3$).

EXAMPLE 6a

Preparation of [3-(3-tert-butoxycarbonylamino-propoxy)pyridin-2-yl]trimethylammonium trifluoromethanesulphonate The procedure described above in Example 1 is used, with 2-dimethylamino-3-hydroxypyridine (0.250 g; molecular mass: 138.17; 1.8 mmol), to give 0.290 g of the tert-butyl ester of [3-(2-dimethylaminopyridin-3-yloxy)propyl]carbamic acid (58%) in the form of a yellow oil after flash chromatography (eluent: heptane/EtOAc: from 70/30 to 50/50).

Rf (CH$_2$Cl$_2$/EtOAc: 50/50): 0.30. $^1$H NMR (CD$_2$Cl$_2$, 298 K): δ: 7.79 (dd, J: 4.0 & 1.5 Hz, 1H); 7.00 (dd, J: 7.8 & 1.2 Hz, 1H); 6.73 (dd, J: 7.8 & 4.8 Hz, 1H); 5.15 (b, w$_{1/2}$: 15 Hz, 1H); 4.02 (t, J: 6.0 Hz, 2H); 3.30 (q, J: 6.0 Hz, 2H); 2.95 (s, 6H); 1.99 (q$^5$, J: 6.0 Hz, 2H); 1.42 (s, 9H). $^{13}$C NMR (CD$_2$Cl$_2$, 298 K): δ: 156.2 (C); 153.7 (C); 146.2 (C); 139.0 (CH); 118.8 (CH); 115.9 (CH); 79.1 (C); 67.4 (CH$_2$); 41.1 (CH$_3$); 38.8 (CH$_2$); 32.3 (CH$_2$); 28.5 (CH$_3$).

The tert-butyl ester of [3-(2-dimethylamino-pyridin-3-yloxy)propyl]carbamic acid is subsequently diluted in toluene (2 ml per 100 mg of ester) and the solution is cooled to 0° C. (ice bath). This solution is admixed with methyl trifluoromethanesulphonate (50 microlitres per 100 mg of ester) and the reaction mixture is stirred at 0° C. for 1 hour. The precipitate of [3-(3-tert-butoxycarbonylaminopropoxy)pyridin-2-yl]-trimethylammonium trifluoromethanesulphonate is filtered off, washed with small portions of ethyl ether and dried under vacuum to give a fine white powder (145 mg per 100 mg of ester).

$^1$H NMR (CD$_2$Cl$_2$, 298 K): δ: 8.09 (dd, J: 3.3 & 1.0 Hz, 1H); 7.67 (bd, J: 8.0 Hz, 1H); 7.61 (dd, J: 7.0 & 4.2 Hz, 1H); 5.20 (b, w$_{1.2}$: 15 Hz, 1H); 4.31 (t, J: 6.3 Hz, 2H); 3.71 (s, 9H); 3.31 (q, J: 6.3 Hz, 2H); 2.12 (q$^5$, J: 6.3 Hz, 2H); 1.38 (s, 9H).
$^{13}$C NMR (CD$_2$Cl$_2$, 298 K): δ: 156.6 (C); 147.7 (C); 142.6 (C); 139.0 (CH); 129.0 (CH); 124.6 (CH); 121.2 (q, J: 319 Hz, CF$_3$); 79.3 (C); 68.1 (CH$_2$); 54.8 (CH$_3$); 37.5 (CH$_2$); 30.0 (CH$_2$); 28.4 (CH$_3$).

EXAMPLE 7

In this example the preparation is described of a compound according to the invention, which is 1-[3-(2-[$^{18}$F]fluoropyridin-3-yloxy)propyl]pyrrole-2,5-dione.

a) K[$^{18}$F]F—K$_{222}$ Complex

In order to recover and recycle the [$^{18}$O]water target, it is passed through an anion exchange resin (AGlx8 from Bio-Rad, 100-200 mesh). The [$^{18}$F]fluoride ion is then eluted from the resin, using 1.0 ml of an aqueous 4.5 mg/ml K$_2$CO$_3$ solution.

Following addition of 11.0 to 15.0 mg of Kryptofix® K$_{222}$ (4,7,13,16,21,24-hexaoxa-1,10-diaza-bicyclo[8.8.8]hexacosane), the resulting solution is then gently concentrated to dryness at 145-150° C. under a stream of nitrogen for 10 minutes, to give a pure K[$^{18}$F]F—K$_{222}$ complex, in the form of a semi-solid white residue.

b) 1-[3-(2-[$^{18}$F]Fluoropyridin-3-yloxy)propyl]-pyrrole-2,5-dione

Freshly distilled DMSO (600 μl), containing 4.0 to 6.0 mg of the "nitro" labelled precursor (tert-butyl ester of [3-(2-nitropyridin-3-yloxy)propyl]carbamic acid), is added directly to the tube containing the dried K[$^{18}$F]-K$_{222}$ complex. The tube (unsealed) is then placed in a heating block (at 145° C. for 4 minutes). The tube is subsequently cooled using an ice/water bath and the remaining radioactivity is measured.

85% to 95% of the initial activity placed in the container is still present. The reaction mixture obtained, which is dark in colour, is then analysed by radiochromatography. The incorporation yields are calculated from the TLC radiochromatogram and are defined by the ratio of surface area of the tert-butyl ester derivative of [3-(2-[$^{18}$F]fluoropyridin-3-yloxy)-propyl]carbamic acid to the total fluorine-18 ($^{18}$F) activity (SiO$_2$-TLC; eluent: EtOAc; Rf: 0.75 and Rf: [$^{18}$F] fluoride ion: 0.0). The reaction mixture is diluted with 1 ml of water and transferred to a C18 Sep-pak cartridge (Waters). The tube is rinsed twice with 1 ml of water, which is also transferred and added to the dilute reaction mixture in the cartridge.

Subsequently the entire system is passed through the cartridge. The cartridge is washed with 3 ml of water and partly dried for 0.5 minute, during which a stream of nitrogen is passed through.

The tert-butyl ester derivative of [3-(2-[$^{18}$F]-fluoropyridin-3-yloxy)propyl]carbamic acid is eluted from the cartridge with 3 ml of dichloromethane into a reaction flask containing 0.1 ml of TFA. 2 times 1 ml of dichloromethane are used to wash the cartridge and to effect complete transfer of the abovementioned [$^{18}$F]-labelled derivative (5% of the total amount of radio-activity, involved in the fluorination process, remains in the cartridge). The incorporation yield is also confirmed, after the elution of the Sep-pak, by the ratio of the CH$_2$Cl$_2$ counting values to total radio-activity eluted (DMSO/H$_2$O+CH$_2$Cl$_2$). The resulting solution, CH$_2$Cl$_2$/TFA (50/1, v/v), is concentrated to dryness (at 65-75° C.) under a moderate stream of nitrogen for 4 to 6 minutes. The yield of the deprotection is quantitative: no above described molecule protected with BOC can be detected by radio-chromatography. The above residue is redissolved in 2 ml of CH$_2$Cl$_2$ and concentrated to dryness again in order to minimize the presence of TFA (at 65-75° C. under a moderate stream of nitrogen for 4 to 6 minutes). The residue is then diluted with 0.5 ml of xylene containing 25 mg of N-methoxycarbonylmaleimide. The container is then hermetically sealed, heated at 190° C. (strong reflux) for 5 minutes and then cooled for 2 minutes, using an ice/water bath. The reaction mixture is then injected into a semi-preparative HPLC column. Isocratic elution [eluent: heptane/EtOAc: 50/50; flow rate: 6.0 ml/minute] gives pure, labelled 1-[3-(2-[$^{18}$F]fluoropyridin-3-yloxy)propyl]pyrrole-2,5-dione; retention time: 7.5 to 8.0 minutes.

Typically, 60 to 70 mCi of pure, labelled 1-[3-(2-[$^{18}$F] fluoropyridin-3-yloxy)propyl]pyrrole-2,5-dione can be obtained in 75 to 85 minutes, from 550-650 mCi of an [$^{18}$F]F$^-$ production batch from a cyclotron.

EXAMPLE 7a

The fluorine-18-labelled compound, 1-[3-(2-[$^{18}$F]fluoropyridin-3-yloxy)propyl]pyrrole-2,5-dione, may also be prepared by repeating steps a) and b) of the process described in Example 7, still using as labelling precursor the "nitro" compound (tert-butyl ester of [3-(2-nitropyridin-3-yloxy)propyl] carbamic acid), but by modifying the final part of the preparation (step c)) as follows (variant according to which step c) is carried out in a two-phase mixture of dioxane and aqueous sodium bicarbonate).

Following deprotection of the amine function (TFA/CH$_2$Cl$_2$) the residue obtained after concentration to dryness is taken up in 0.250 ml of dioxane containing 25 mg of N-methoxycarbonylmaleimide. This solution is admixed with 0.750 ml of a saturated aqueous sodium bicarbonate solution and the preparation is vortexed at ambient temperature for 10 minutes. The reaction mixture is subsequently diluted with 1 ml of water and transferred to a C18 Sep-pak cartridge (Waters). The flask is rinsed twice with 1 ml of water, which is likewise transferred and added to the dilute reaction mixture in the cartridge. Finally 8 ml of water are also added to the dilute reaction mixture in the cartridge. The system is subsequently passed into the cartridge. The cartridge is washed with 3 ml of water and partly dried for 0.5 minute, during which a stream of nitrogen is passed through. The fluorine-18-labelled derivative (1-[3-(2-[$^{18}$F]fluoropyridin-3-yloxy) propyl]-pyrrole-2,5-dione) is eluted from the cartridge with 3 ml of dichloromethane in a new, empty flask. Two times 1 ml of dichloromethane are used to wash the cartridge and to effect complete transfer of the [$^{18}$F]-labelled derivative mentioned above. The solution containing the [$^{18}$F]-labelled derivative mentioned above is concentrated (at 65-75° C., under a moderate stream of nitrogen, for 3 to 5 minutes) to a volume of approximately 1 ml and injected into a semi-preparative HPLC column. Purification is identical to that described in Example 7.

EXAMPLE 7b

The fluorine-18-labelled compound, 1-[3-(2-[$^{18}$F]fluoropyridin-3-yloxy)propyl]pyrrole-2,5-dione, may also be prepared by repeating steps a) and b) of the process described in Example 7 or 7a, but using, as labelling precursor, the "trimethylammonium trifluoromethanesulphonate" compound ([3-(3-tert-butoxycarbonylaminopropoxy)pyridin-2-yl]trimethylammonium trifluoromethanesulphonate).

EXAMPLE 8

In this example the labelling of a peptide is described, namely the peptide N-acetyl-Lys-Ala-Ala-Ala-Ala-Cys-amide, with a compound according to the invention, which is 1-[3-(2-[$^{18}$F]fluoropyridin-3-yloxy)-propyl]pyrrole-2,5-dione.

The procedure is as follows:

One equivalent of peptide (2 mg/ml; 200 nmol; 36.2 µl) in solution in 50 mM Tris, 150 mM NaCl buffer, pH=7.4 is admixed with 1 equivalent of TCEP in Tris buffer (7.9 mg/ml; 7.3 µl; 200 nmol). The sample is left at ambient temperature for 5 minutes and then diluted in 1 ml of Tris buffer. The dry synthon, 1-[3-(2-[$^{18}$F]fluoropyridin-3-yloxy)propyl]pyrrole-2,5-dione, is taken up in 100 µl of a 50/50 heptane/ethyl acetate mixture, and the solution of reduced peptide is added. The sample is left at ambient temperature for 10 minutes, stirring from time to time. The labelled peptide is purified by HPLC on a C18 column with a gradient from 0 to 34% acetonitrile/0.1% TFA in H$_2$O/0.1% TFA over 30 minutes (DeltaPak C18 column, R$_{t\text{-}peptide}$=28 min)

The invention claimed is:

1. A compound according to formula (I):

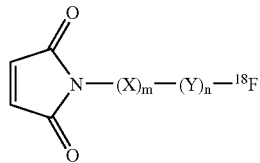

(I)

wherein
m represents an integer from 0 to 10;
n represents an integer from 1 to 10;
Y represents a monocyclic or bicyclic heterocyclic group selected from the group consisting of imidazolyl, pyrazolyl, benzimidazolyl, pyridinyl, pyridazinyl, pyrimidinyl, pyrazinyl, triazinyl, quinolinyl, isoquinolinyl, cinnolinyl, quinazolinyl, quinoxalinyl and purinyl, wherein Y may optionally be substituted with one or more substituents selected from the group consisting of hydrogen, halogen, phenyl, C$_1$-C$_6$ alkyl, C$_1$-C$_6$ alkoxy, aryloxy, amino, mono- or di(C$_1$-C$_6$ alkyl)amino, mono- or di(aryl)amino, thio, C$_1$-C$_6$ alkylthio, arylthio, formyl, C$_1$-C$_6$ alkyl-carbonyl, arylcarbonyl, carbonyl, C$_1$-C$_6$ alkoxy-carbonyl, aryloxycarbonyl, C$_1$-C$_6$ alkylamino-carbonyl, arylaminocarbonyl and trifluoromethyl; and
X represents a radical of the following formula:

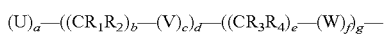

wherein
a, b, c, d, e, f and g each independently represent an integer from 0 to 10; and
U, V and W each independently represent —NR$_1$—, —O—, —S—, —N(—O)—, ethynyl, —CR$_1$=CR$_2$—, —C(=O)—, —C(=S)—, —C(=NR$_1$)—, —C(=O)O—, —C(=S)S—, —C(=NR$_1$)NR$_2$—, —CR$_1$R$_2$—, —CR$_1$OR$_2$— or —CR$_1$NR$_2$R$_3$—, wherein R$_1$, R$_2$, R$_3$ and R$_4$ are each independently selected from the group consisting of hydrogen, halogen, phenyl, C$_1$-C$_6$ alkyl, C$_1$-C$_6$ alkoxy, aryloxy, amino, mono- or di(C$_1$-C$_6$ alkyl)amino, mono- or di(aryl)amino, thio, C$_1$-C$_6$ alkylthio, arylthio, formyl, C$_1$-C$_6$ alkyl-carbonyl, arylcarbonyl, carbonyl, C$_1$-C$_6$ alkoxy-carbonyl, aryloxycarbonyl, C$_1$-C$_6$ alkylamino-carbonyl, arylaminocarbonyl and trifluoromethyl.

2. The compound according to claim 1, wherein n is 1 and Y is a 3-pyridinyl group.

3. The compound according to claim 2, wherein the compound is represented by formula (II):

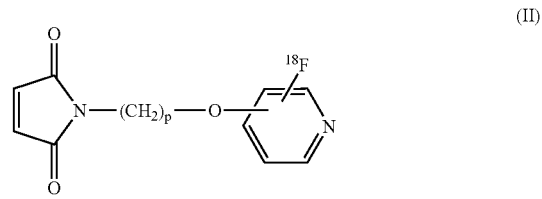

(II)

wherein p represents an integer from 1 to 10.

4. The compound according to claim 3, wherein the compound is selected from the group consisting of:
1-[2-(2-[$^{18}$F]fluoropyridin-3-yloxy)ethyl]-pyrrole-2,5-dione;
1-[4-(2-[$^{18}$F]fluoropyridin-3-yloxy)butyl]-pyrrole-2,5-dione;
1-[5-(2-[$^{18}$F]fluoropyridin-3-yloxy)pentyl]-pyrrole-2,5-dione;
1-[6-(2-[$^{18}$F]fluoropyridin-3-yloxy)hexyl]-pyrrole-2,5-dione;
1-[(2-[$^{18}$F]fluoropyridin-3-yloxy)methyl]-pyrrole-2,5-dione; and
1-[3-(2-[$^{18}$F]fluoropyridin-3-yloxy)propyl]-pyrrole-2,5-dione.

5. The compound according to claim 2, wherein the compound is represented by formula (III):

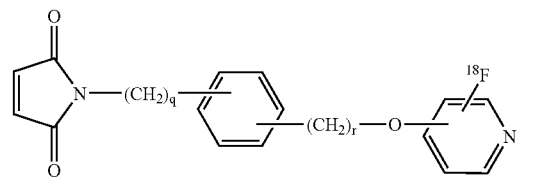

(III)

wherein q and r each independently represent an integer from 0 to 10.

6. The compound according to claim 5, wherein the compound is selected from the group consisting of:
1-{4-[2-(2-[$^{18}$F]fluoropyridin-3-yloxy)-ethyl]phenyl}pyrrole-2,5-dione;
1-[4-(2-[$^{18}$F]fluoropyridin-3-yloxymethyl)-phenyl]pyrrole-2,5-dione; and
1-[4-(2-[$^{18}$F]fluoropyridin-3-yloxymethyl)-benzyl]pyrrole-2,5-dione.

7. The compound according to claim 2, wherein the compound is represented by formula (IV):

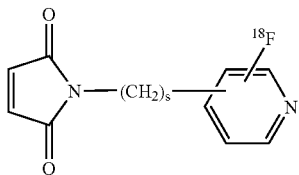

wherein s represents an integer from 1 to 10.

8. The compound according to claim 7, wherein the compound is 1-[3-(6-[$^{18}$F]fluoropyridin-3-yl)propyl]-pyrrole-2,5-dione.

9. The compound according to claim 2, wherein the compound is represented by formula (V):

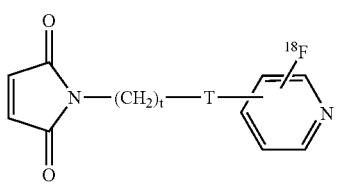

wherein t represents an integer from 0 to 10; and T is a —CH═CH— group or a —C≡C— group.

10. The compound according to claim 9, wherein the compound is selected from the group consisting of:
1-[3-(6-[$^{18}$F]fluoropyridin-3-yl)allyl]-pyrrole-2,5-dione; and
1-[3-(6-[$^{18}$F]fluoropyridin-3-yl)prop-2-ynyl]pyrrole-2,5-dione.

11. A kit comprising a macromolecule and the compound according to claim 1.

12. The kit according to claim 11, wherein the kit is a detection and analysis kit for medical imaging.

13. The kit according to claim 11, wherein the kit is a diagnosis kit.

14. The kit according to claim 11, wherein the macromolecule is a biological macromolecule.

15. The kit according to claim 11, wherein the macromolecule is a biological macromolecule selected from the group consisting of an oligonucleotide, a protein, an antibody and a peptide.

16. The kit according to claim 11, wherein the macromolecule is a macromolecule for recognition of a specific site that exhibits target molecules associated with a particular disease.

17. The kit according to claim 11, wherein the macromolecule is a macromolecule for recognition of a specific site that is selected from the group consisting of apoptosis sites, necrosis sites or tumor sites.

18. A process for preparing the compound according to claim 1, wherein the process comprises:
contacting a precursor compound according to formula (Ia):

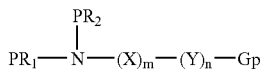

wherein

PR$_1$ and PR$_2$ each independently represent: a hydrogen or a protective group, with the proviso that PR$_1$ and PR$_2$ are not both a hydrogen; or PR$_1$ and PR$_2$, together with the nitrogen atom, form a cyclic protective group;

Gp represents a leaving group capable of being replaced by a fluorine-18 atom;

m represents an integer from 0 to 10;

n represents an integer from 1 to 10;

Y represents a monocyclic or bicyclic heterocyclic group selected from the group consisting of imidazolyl, pyrazolyl, benzimidazolyl, pyridinyl, pyridazinyl, pyrimidinyl, pyrazinyl, triazinyl, quinolinyl, isoquinolinyl, cinnolinyl, quinazolinyl, quinoxalinyl and purinyl, wherein Y may optionally be substituted with one or more substituents selected from the group consisting of hydrogen, halogen, phenyl, C$_1$-C$_6$ alkyl, C$_1$-C$_6$ alkoxy, aryloxy, amino, mono- or di(C$_1$-C$_6$ alkyl)amino, mono- or di(aryl)amino, thio, C$_1$-C$_6$ alkylthio, arylthio, formyl, C$_1$-C$_6$ alkyl-carbonyl, arylcarbonyl, carbonyl, C$_1$-C$_6$ alkoxy-carbonyl, aryloxycarbonyl, C$_1$-C$_6$ alkylaminocarbonyl, arylaminocarbonyl and trifluoromethyl; and X represents a radical of the following formula:

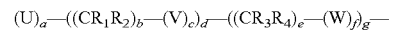

wherein a, b, c, d, e, f and g each independently represent an integer from 0 to 10; and U, V and W each independently represent —NR$_1$—, —O—, —S—, —N(—O)—, ethynyl, —CR$_1$═CR$_2$—, —(C═O)—, —(C═S)—, —C(═NR$_1$)—, —C(═O)O—, —(C═S)S—, —C(═NR$_1$)NR$_2$—, —CR$_1$R$_2$—, —CR$_1$OR$_2$— or —CR$_1$NR$_2$R$_3$—, wherein R$_1$, R$_2$, R$_3$ and R$_4$ are each independently selected from the group consisting of hydrogen, halogen, phenyl, C$_1$-C$_6$ alkyl, C$_1$-C$_6$ alkoxy, aryloxy, amino, mono- or di(C$_1$-C$_6$ alkyl)amino, mono- or di(aryl)amino, thio, C$_1$-C$_6$ alkylthio, arylthio, formyl, C$_1$-C$_6$ alkyl-carbonyl, arylcarbonyl, carbonyl, C$_1$-C$_6$ alkoxy-carbonyl, aryloxycarbonyl, C$_1$-C$_6$ alkylamino-carbonyl, arylaminocarbonyl and trifluoromethyl.

with a source of [$^{18}$F]-labeled fluoride anions (F) to provide a compound according to formula (Ib):

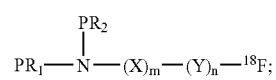

removing the protective group(s) PR$_1$ and/or PR$_2$ from the compound according to formula (Ib) to provide a compound according to formula (Ic):

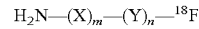

reacting the compound according to formula (Ic) with a reactant capable of providing a maleimido group from an amino group, to yield the compound according to claim 1.

19. The process according to claim 18, wherein the protective group(s) PR$_1$ and/or PR$_2$ is/are selected from the group consisting of tert-butoxycarbonyl (BOC) and fluorenylmethoxycarbonyl (FMOC).

20. The process according to claim 18, wherein the protective groups PR$_1$ and PR$_2$, together with the nitrogen atom, form a phthalamido protective group.

21. The process according to claim 18, wherein Gp is selected from the group consisting of a halogen, a mesyl group, a tosyl group, a triflate group, a nitro group and an ammonium salt.

22. The process according to claim 21, wherein Gp is an ammonium salt and the ammonium salt is trimethylammonium trifluoromethanesulphonate.

23. The process according to claim 18, wherein the source of [18F]-labeled fluoride anions (F) comprises the fluoride anions (F) and a counterion.

24. The process according to claim 23, wherein the counterion is a cation selected from the group consisting of rubidium, tetrabutylammonium, potassium, sodium and lithium.

25. The process according to claim 23, wherein the counterion is a cation selected from the group consisting of potassium, sodium and lithium, and the cation is stabilized by a cryptand or a crown ether.

26. The process according to claim 18, wherein said removing is carried out by deprotecting the compound according to formula (Ib) with trifluoroacetic acid (TFA) in a solvent for a period of 1-5 minutes to provide the compound according to formula (Ic).

27. The process according to claim 26, wherein the solvent is dichloromethane.

28. The process according to claim 18, wherein the reactant capable of providing a maleimido group from an amino group is selected from the group consisting of N-methoxycarbonylmaleimide and succinimide.

29. The process according to claim 18, wherein said reacting is carried out in a solvent with heating at a temperature of 100-200° C. for a period of 1-20 minutes.

30. The process according to claim 29, wherein the solvent is xylene or tetrahydrofuran.

31. The process according to claim 18, wherein said reacting is carried out in a two-phase mixture at ambient temperature for a period of 3-15 minutes.

32. The process according to claim 31, wherein the two-phase mixture comprises dioxane and aqueous sodium bicarbonate.

33. The process according to claim 18, wherein the precursor compound according to formula (Ia) corresponds to a compound according to formula (IIa):

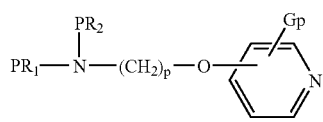

(IIa)

wherein p represents an integer from 1 to 10.

34. The process according to claim 18, wherein the precursor compound according to formula (Ia) corresponds to a compound according to formula (IIb):

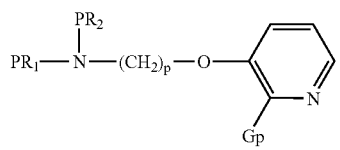

(IIb)

wherein p represents an integer from 1 to 10.

35. The process according to claim 18, wherein the precursor compound according to formula (Ia) corresponds to a compound according to formula (IIIa):

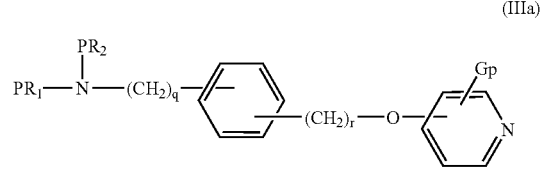

(IIIa)

wherein q and r each independently represent an integer from 0 to 10.

36. The process according to claim 18, wherein the precursor compound according to formula (Ia) corresponds to a compound according to formula (IIIb):

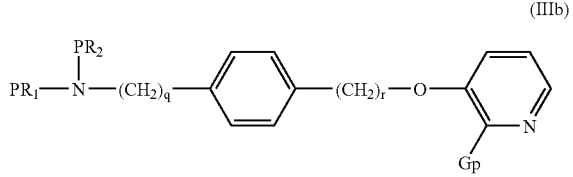

(IIIb)

wherein q and r each independently represent an integer from 0 to 10.

37. The process according to claim 18, wherein the precursor compound according to formula (Ia) corresponds to a compound according to formula (IVa):

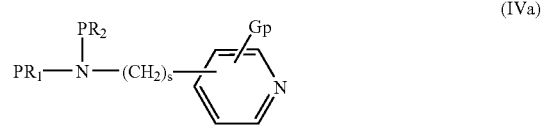

(IVa)

wherein s represents an integer from 1 to 10.

38. The process according to claim 18, wherein the precursor compound according to formula (Ia) corresponds to a compound according to formula (IVb):

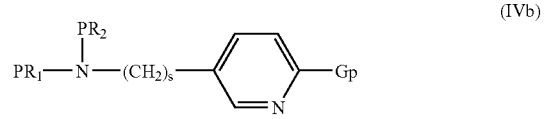

(IVb)

wherein s represents an integer from 1 to 10.

39. The process according to claim 18, wherein the precursor compound according to formula (Ia) corresponds to a compound according to formula (Va):

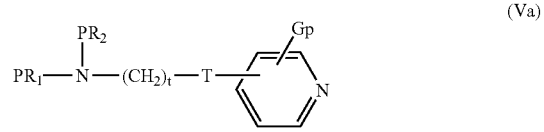

(Va)

wherein t represents an integer from 0 to 10; and T is a —CH═CH— group or a —C≡C— group.

40. The process according to claim 18, wherein the precursor compound according to formula (Ia) corresponds to a compound according to formula (Vb):

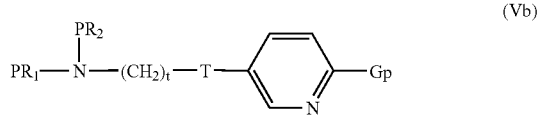

(Vb)

wherein t represents an integer from 0 to 10; and T is a —CH═CH— group or a —C≡C— group.

41. A method of labeling a macromolecule comprising coupling the compound according to claim 1 to the macromolecule.

42. The method according to claim 41, wherein the macromolecule is a biological macromolecule.

43. The method according to claim 41, wherein the macromolecule is a biological macromolecule selected from the group consisting of an oligonucleotide, a protein, an antibody and a peptide.

44. The method according to claim 41, wherein the macromolecule is a macromolecule for recognition of a specific site that exhibits target molecules associated with a particular disease.

45. The method according to claim 41, wherein the macromolecule is a macromolecule for recognition of a specific site that is selected from the group consisting of apoptosis sites, necrosis sites or tumor sites.

* * * * *